United States Patent [19]

Iwama et al.

[11] Patent Number: 5,545,299

[45] Date of Patent: Aug. 13, 1996

[54] VAPOR PHASE SENSOR

[75] Inventors: Akifumi Iwama; Masahiro Iseki; Azusa Nakagawa, all of Tsukuba, Japan

[73] Assignee: Sanyo Electric Co., Inc., Osaka, Japan

[21] Appl. No.: 551,865

[22] Filed: Nov. 21, 1995

Related U.S. Application Data

[62] Division of Ser. No. 305,157, Sep. 13, 1994, Pat. No. 5,496,451.

[30] Foreign Application Priority Data

| Sep. 13, 1993 | [JP] | Japan | 5-228611 |
| Sep. 14, 1993 | [JP] | Japan | 5-228612 |
| Sep. 14, 1993 | [JP] | Japan | 5-228613 |
| Jun. 29, 1994 | [JP] | Japan | 6-148013 |

[51] Int. Cl.⁶ .................................. G01N 27/26
[52] U.S. Cl. .................... 204/412; 204/424; 204/431; 422/83; 422/84; 422/98
[58] Field of Search .................. 204/412, 424, 204/431; 422/83, 84, 98

[56] References Cited

U.S. PATENT DOCUMENTS

| 3,824,168 | 7/1974 | Oswin et al. | 204/412 |
| 5,239,258 | 8/1983 | Kauffman | 324/71.1 |

FOREIGN PATENT DOCUMENTS

| 5-10905 | 1/1993 | Japan . |
| 5-45321 | 2/1993 | Japan . |
| 5-60727 | 3/1993 | Japan . |

OTHER PUBLICATIONS

Slater, Jonathan, M., et al. "Examination of Ammonia–Poly (pyrrole) Interactions by Piezoelectric and Conductivity Measurements", Analyst, Nov. 1991, vol. 116., pp. 1125–1131.

Slater, Jonathan, M., et al. "Gas and Vapour Detection With Poly (pyrrole) Gas Sensors", Analyst, Aug. 1992, vol. 117, pp. 1265–1271.

Slater, Jonathan, M., et al. "Multi-layer Conducting Polymer Gas Sensor Arrays for Olfactory Sensing", Analyst, Apr. 1993, vol. 118, pp. 379–384.

Hartnett, Margaret, et al. "Detector Based on Charge Coupled Device Technology", Analytical Proceedings, Feb. 1992, vol. 29, pp. 52–57.

Primary Examiner—Bruce F. Bell
Attorney, Agent, or Firm—Loeb & Loeb LLP

[57] ABSTRACT

On the bottom face of a measurement section, measurement electrodes and a reference electrode are formed and a solution supply pipe is opened. Then, if a predetermined electrolytic solution is supplied from the solution supply pipe, the electrolytic solution can be held on an electrolytic solution holding surface on the lower end of the measurement section, utilizing the with surface tension thereof for providing a gas reception portion. Since the electrolytic solution is exposed directly to the air, substances in a vapor phase (particularly, odor substances) are diffused into the electrolytic solution, causing an electric state to change. The substances in the vapor phase can be detected by detecting the electric state change. The electrolytic solution held on the lower face of the measurement section can be updated by further supplying more electrolytic solution.

8 Claims, 18 Drawing Sheets

| Parameters | Ethanol | Acetone | Ethyl acetate | N,N-Dimethyl formamide |
|---|---|---|---|---|
| P1(=m2) | 0.743 | 0.072 | 0.717 | 0.109 |
| P2(=m3/lm1l) | 0.811 | 1.135 | 0.968 | 1.002 |
| P3(=m4) | 0.124 | 0.132 | 0.099 | 0.038 |
| P4(=m5/lm1l) | 4.982 | 9.127 | 0.416 | -3.625 |
| P5(=m6) | 16.208 | 5.516 | 3.256 | 8.785 |

Parameter of substance A (2-heptanone)
P1 = 0.069, P2 = 1.900, P3 = 0.925, P4 = 9.069, P5 = 2.966

Parameter of substance B (*N,N*-Dimethylacetamide)
P1 = 0.130, P2 = 1.124, P3 = 0.028, P4 = -4.550, P5 = 8.340

VAPOR PHASE SENSOR

This is a divisional of application Ser. No. 08/305,157, filed Sep. 13, 1994, now U.S. Pat. No. 5,496,451.

BACKGROUND OF THE INVENTION

1. Field of the Invention

This invention relates to a method and a sensor for detecting chemical substances contained in a vapor phase.

2. Description of the Related Art

Hitherto, gas chromatography, etc., has been used to detect substances contained in a vapor phase, and various substance concentrations in a sampled gas are detected. However, the chromatography method basically requires that human beings should sample specimens. It is not suited for automatically detecting substances in a vapor phase.

A vapor phase sensor is known which comprises a plurality of electrodes, whose electrical conditions (normally, potential and current depending on oxidation-reduction potential change) change according to the substance concentration, etc., in a phase. The electrodes are installed in a vapor phase and the electrical conditions of the electrodes are detected for determining the substance amount in the vapor phase. Such a vapor phase sensor can be used to detect the concentration of any desired gas simply by installing the sensor in the detected atmosphere. The concentration of the gas to be measured can also be measured by using films, membranes, etc., having gas selectivity.

Such vapor phase sensors are described in Japanese Patent Laid-Open Nos. Hei 5-10905, 5-60727, 5-45321, etc., for example.

However, in detection of chemical substances by such conventional sensors, basically only a potential or current change is measured. The concentration of a single gas or a total potential or current change of gases can only be measured by one sensor, and substances contained in a vapor phase cannot be identified.

By the way, freshness of various foods is often estimated from factors such as the storage condition (freezing, cold storage) and the number of storage days of the foods. On the other hand, very fresh beef is not necessarily good while mature beef is preferred as food. In the final stage of the distribution process, frozen beef is not simply thawed, but placed under control at predetermined temperature and humidity in a thawing and maturing chamber for providing mature beef.

However, the degree of maturity varies depending on the condition of the frozen beef before its freezing, etc. At this time, human beings inspect the condition of thawed beef to determine the degree of maturity. Such judgement by human beings leads to inefficient work and moreover varies depending on the individual. Therefore, it is desired to measure the degree of maturity (freshness) easily and rapidly.

The measurement needs to be made while being out of contact with the food to comply with regard to the food hygiene management laws etc., and in such a way that the food is not destroyed while being measured during quality control.

SUMMARY OF THE INVENTION

It is therefore an object of the invention to provide a detection method capable of identifying chemical substances contained in a vapor phase.

It is another object of the invention to provide a vapor phase sensor capable of specifying substances contained in a vapor phase.

It is a further object of the invention to provide a method of measuring the freshness of food stuffs, such as beef, efficiently in noncontact and nondestructive conditions.

To these ends, according to the invention, there is provided a method of detecting a chemical substance in a vapor phase comprising the steps of holding an electrolytic solution, having a surface coming into direct contact with a vapor phase, around electrodes, diffusing a chemical substance in the vapor phase into the electrolytic solution, and detecting an electric state at the electrodes existing in the electrolytic solution as a change with time based on the diffusion and absorption of the chemical substance on the electrodes, wherein the chemical substance in the vapor phase is detected based on the detected change with time.

The step of holding the electrolytic solution around the electrodes is effected by using surface tension thereof, and an electrolytic solution is supplied from an electrolytic solution reservoir for holding the new electrolytic solution, thereby repeating detection.

The chemical substance detection method according to the invention detects a change with time of the electric state caused by a chemical substance in a vapor phase diffusing into an electrolytic solution held. The change with time varies depending on the chemical substance. Then, a specific chemical substance can be identified according to the change pattern.

If the electrolytic solution is held using surface tension, the electrolytic solution can be updated by supplying a new electrolytic solution, thus an analysis on a new pattern and identification of a chemical substance can be repeated.

According to the invention, there is provided a method of identifying a chemical substance contained in a vapor phase comprising the steps of (A) holding an electrolytic solution, having a surface coming into direct contact with a vapor phase, around electrodes, (B) obtaining a predetermined fitting function and parameters from a chemical substance selected as a reference substance, the step comprising the steps of (b1) diffusing the chemical substance selected as the reference substance into the electrolytic solution, (b2) detecting an electric state at the electrodes existing in the electrolytic solution as a change with time based on the diffusion and absorption of the chemical substance on the electrodes and preparing a pattern of change of the electric state with time, and (b3) setting a fitting function based on the pattern and finding parameters of the reference substance for the fitting function, (C) obtaining predetermined parameters from a chemical substance being measured, the step comprising the steps of (c1) diffusing the chemical substance being measured into the electrolytic solution, and (c2) detecting an electric state at the electrodes existing in the electrolytic solution as a change with time based on the diffusion and absorption of the chemical substance on the electrodes and preparing parameters of the substance being measured for the fitting function, and (D) calculating a distance between the parameters of the reference substance and the parameters of the substance being measured and determining that the reference substance having the minimum distance therebetween is most similar to the substance being measured.

In the chemical substance identification method as described above, a similarity between electric state change patterns with time is quantified and the degree of similarity between chemical substances is determined based on the quantified value. Specifically, the electric state change patterns with time are compared with each other by calculating the distance between the parameters for one pattern and those for the other pattern for a fitting function. The similarity between the patterns is quantified as the distance between the parameters.

According to the chemical substance identification method according to the invention, patterns of reference substances and substances being measured (electric state change patterns with time) are prepared by using the detection method of the invention mentioned above. A proper fitting function is derived from the patterns of the different reference substances. At the same time, the parameters of the reference substances are calculated for the fitting function. On the other hand, the parameters of the chemical substance being measured are also calculated for the fitting function. The distance between the parameters of the reference substances and the parameters of the substance being measured is calculated. It is determined that the reference substance having the minimum distance therebetween is most similar to the substance being measured. For example, it is determined that the measured substance having parameters close to the parameters of ethanol is a compound similar to ethanol and that the substance having parameters far from those of ethanol is not similar to ethanol. Of course, if the substance has the same parameters as ethanol, it is identified as ethanol. The distance between parameters can be calculated from n parameters. For example, a method such as a Euclidean distance, squared Euclidean distance, Chebyehev distance, or 1-correlation coefficient calculation method can be used as the distance calculation method between parameters.

According to the invention, there is provided a vapor phase sensor comprising measurement electrodes, a reference electrode, an electrolytic solution holding surface comprising at least the measurement electrodes and the reference electrode for holding an electrolytic solution having an outer surface exposed directly to a vapor phase on surfaces of the measurement electrodes and the reference electrode by using surface tension thereof, a source for supplying an electrolytic solution onto the electrolytic solution holding surface, and a section for detecting an electric state change between the measuring electrodes and the reference electrode caused by a chemical substance in a vapor phase diffusing into the electrolytic solution, wherein the electrolytic solution held on the electrolytic solution holding surface is updated by supplying an electrolytic solution from the electrolytic solution reservoir for detecting a substance in a vapor phase whenever necessary in the updated solution condition.

The vapor phase sensor may further include means for removing an electrolytic solution held on the electrolytic solution holding surface. The removal means can be provided by combining a supply pipe for supplying an electrolytic solution onto the electrolytic solution holding surface and a discharge pipe for discharging the electrolytic solution from the electrolytic solution holding surface.

Further, the surfaces of the measurement electrodes may be made of conducting polymer films. The films made of conducting polymers can be formed with electrochemically polymerized films, etc., for example.

A predetermined amount of an electrolytic solution is held on the electrolytic solution holding surface by supplying the electrolytic solution in the predetermined amount from the electrolytic solution reservoir. Since the surface of the electrolytic solution is exposed directly to the air, chemical substances in a vapor phase are diffused into the electrolytic solution efficiently. Then, the chemical substances can be detected stably based on a potential change between the measurement electrodes and the reference electrode. Since the electrolytic solution held on the electrolytic solution holding surface can be replaced by supplying another electrolytic solution, a change in the atmosphere can also be handled easily and measurement can be made whenever necessary.

If the electrolytic solution cannot easily be replaced due to oversupply of electrolytic solution, for example, when the electrolytic solution holding surface is facing upward, the removal means installed in the vapor phase sensor enables easy replacement of the electrolytic solution for updating the gas reception section.

Further, high-performance detection can be maintained over a long term by making the surface of measurement electrodes of conducting polymer films.

According to the invention, there is provided a method of measuring freshness of food stuffs comprising the steps of installing electrodes in an electrolytic solution into which chemical substances discharged into a vapor phase from a food stuff are diffused, and detecting an electric state of the electrodes and measuring freshness of the food stuff based on a change in the electric state of the electrodes obtained.

The food stuff may be beef. The films attached on the electrode surface may be made of conducting polymer films.

Thus, according to the invention, chemical substances contained in a vapor phase discharged from food, such as odor substances, are diffused into an electrolytic solution or absorbed on the electrodes, causing the electric state of the electrodes to change, and the freshness of food is measured in response to the electric state change of the electrodes. Thus, measurement can be made without intervention of human beings, and freshness can be measured objectively. Particularly, it was difficult to measure freshness (maturity degree) of beef with conventional measuring instruments, but the invention makes it possible to measure it. Preferably, the surface of measurement electrodes are made of conducting polymers.

DESCRIPTION OF THE PREFERRED EMBODIMENTS

Referring now to the accompanying drawings, there are shown preferred embodiments of the invention.
[Configuration]

Figure 1:
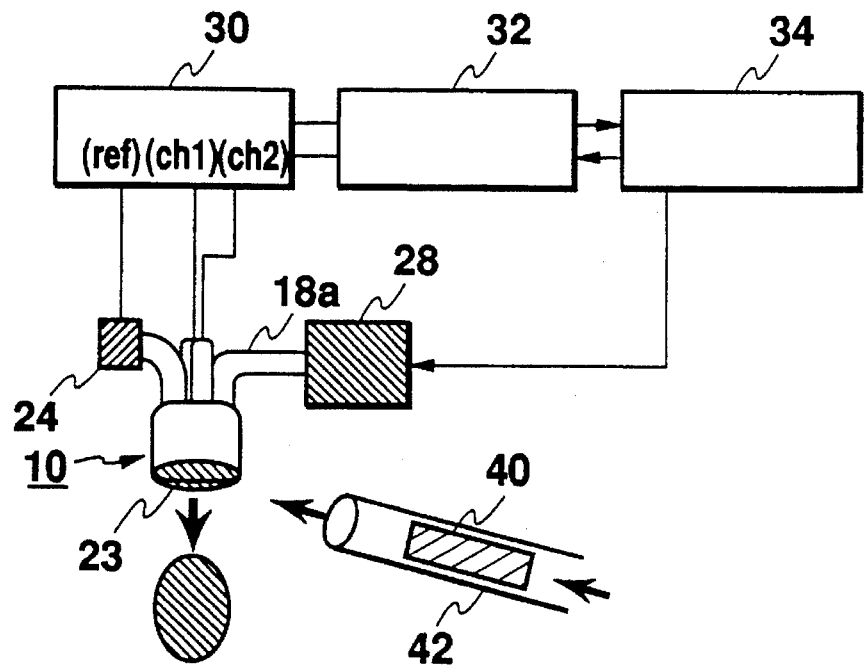
FIG. 1 is a drawing showing the configuration of a preferred vapor phase sensor of the invention.
Figure 2:
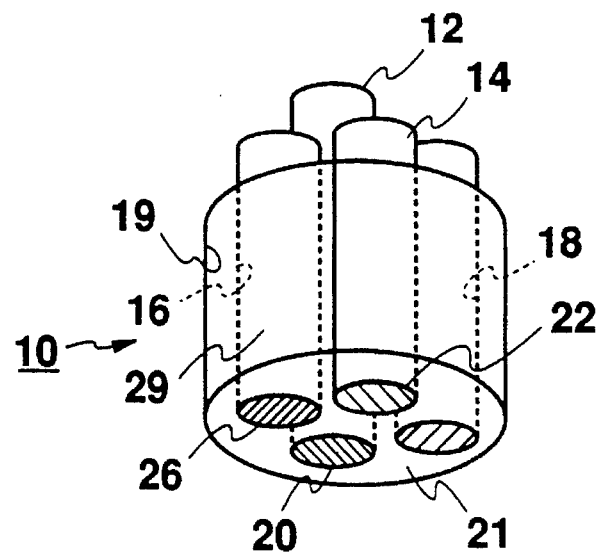
FIG. 2 is a drawing showing the structure of a measurement section 10.

FIG. 1 is a drawing showing the overall configuration of a vapor phase sensor according to the first embodiment of the invention. FIG. 2 is an enlarged view showing the structure of a measurement section 10.

The measurement section 10 comprises two platinum electrodes 12 and 14 and two fluorocarbon resin pipes 16 and 18 fixed with an epoxy resin 19, the lower face of which forms an electrolytic solution holding surface 21. The films attached on first and second measurement electrodes 20 and 22 made of different conducting polymers are formed on the lower faces of the platinum electrodes 12 and 14. That is, in the embodiment, the first measurement electrode 20 made of a PPy/PVS (polypyrrole doped with polyvinyl sulfate ions) film is formed on the lower face of the platinum electrode 12 and the second measurement electrode 22 made of a PPy/Cl (polypyrrole doped with chloride ions) film is formed on the lower face of the platinum electrode 14. The platinum electrodes 12 and 14 may have the lower ends only formed with platinum disks. The conducting polymer films are formed by electrochemical polymerization or chemical polymerization.

A salt bridge 29 made of 3 M (mol/l) KCl (potassium chloride) and 3% agar is installed in the fluorocarbon resin pipe 16 and a silver-silver chloride electrode 24 is fitted to the opposite end of the salt bridge 29, forming a reference electrode 26. Generally, the entire solution containing the silver-silver chloride electrode 24 and chloride ions is called the reference electrode, but the lower end of the salt bridge 29 is called the reference electrode 26 in the embodiment for the description of the operation, etc., because they are substantially the same. On the other hand, the fluorocarbon resin pipe 18 is connected via an electrolytic solution supply tube 18a to an electrolytic solution supply section 28 for supplying an electrolytic solution from the lower end of the fluorocarbon resin pipe 18 to the electrolytic solution holding surface 21. The electrolytic solution supply section 28 consists of a proper fixed displacement pump and a proper solution tank, for example. Therefore, when an electrolytic solution is supplied from the lower end of the fluorocarbon resin pipe 18 to the electrolytic solution holding surface 21, the lower faces of the fluorocarbon resin pipe 18 and the salt bridge 29 are electrically connected, enabling detection of the potential of the electrolytic solution in relation to the reference electrode 26. Although a 1M KCl solution is used as the electrolytic solution in the embodiment, the electrolytic solution should be changed in response to the measurement object. If the measurement object is not water-soluble, a suitable solvent other than water is selected.

Upon supplying of a predetermined amount of electrolytic solution, the electrolytic solution supply section 28 stops supplying the electrolytic solution, and is sealed in fluid-sealing relation. The electrolytic solution is held on the electrolytic solution holding surface 21 consisting of the lower faces of the first and second measurement electrodes 20 and 22 and the two fluorocarbon resin pipes 16 and 18 and the lower face of the epoxy resin 19 by its surface tension, the surface providing a gas reception portion 28, an area directly exposed to a vapor phase.

The silver-silver chloride electrode 24 and the platinum electrodes 12 and 14 are connected to a reference electrode input terminal (ref), channel 1 (ch1), and channel 2 (ch2) of an amplifier 30. The amplifier 30 compares the potential of the reference electrode 26 with the potential of the first and second measurement electrodes 20 and 22 and amplifies the voltage difference for supply to a recorder 32. The amplifier 30 adopts a low-noise DC amplifier.

The recorder 32 records the signals supplied from the amplifier 30. Further, a controller 34 controls supplying of an electrolytic solution by the electrolytic solution reservoir 28 every predetermined time or in response to a predetermined operator input. The controller 34 analyzes the measurement result provided by the recorder 32 and identifies a substance according to a technique described below.

The vapor phase sensor according to the embodiment has the two measurement electrodes 20 and 22 which differ in film composition. Then, a response difference due to the film composition difference can be known by using the first and second measurement electrodes 20 and 22 for simultaneous measurement. On actual measurement, the measurement result of the preferred measurement electrode 20 or 22 can also be used for measurement.
[Measurement operation]

Figure 3:
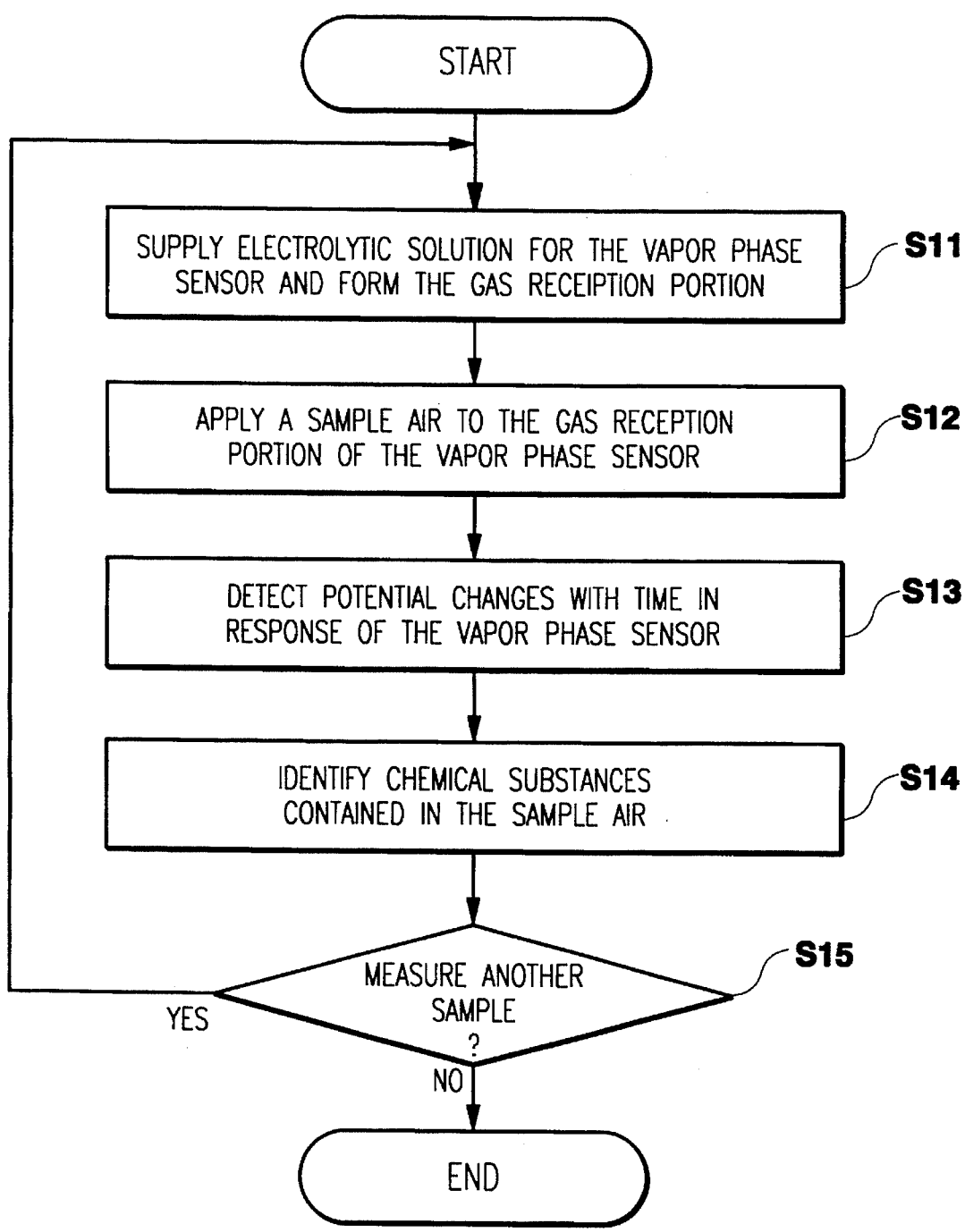
FIG. 3 is a flowchart showing the measurement operation of the vapor phase sensor of the invention.

Detection of chemical substances using the vapor phase sensor described above is described with reference to FIG. 3. First, a predetermined amount of an electrolytic solution is supplied from the electrolytic solution supply section 28 and is held on the electrolytic solution holding surface 21 for forming the gas reception portion 23 at step S11.

Next, air containing a stimulant substance is blown against the gas reception portion 23 for a predetermined time at step S12. This step is performed, for example, as follows: First, 100 µl of a stimulant solution containing a predetermined chemical substance is measured 100 µl and is dropped on to a deodorized filter paper 40 (area 5 cm²). The filter paper 40 is housed In a Pasteur pipette 42 and the rear end of the Pasteur pipette 42 is connected via an odorless tube (not shown) to a pump (not shown).

In this condition, air is fed from the pump to blow the stimulant substance evaporating from the filter paper 40 against the gas reception portion 23 of the vapor phase sensor. The stimulation time for which the stimulant containing gas was blown was 1–20 seconds at a flow velocity of 90 ml/min (air velocity 1.9 m/sec). The stimulation time is controlled by the controller 34 and the flow velocity is monitored with a flow meter and is feedback controlled by the controller 34. A deodorizing tube containing activated carbon and a dehydrating tube containing silica gel are located between the pump and the pipette for using air from which odors and water vapor are removed.

Change with time of the potential difference between the measurement electrodes 20, 22 and the reference electrode is detected on the recorder at step S13. The detection result is sent to the controller 34, which then analyzes the detection result to identify the chemical substance at step S14. One example of the technique for identifying chemical substances is given below.

When one measurement terminates in such a manner, whether or not another measurement is to be made is determined at step S15. If it is to be made, control returns to step S11 at which another electrolytic solution is supplied. Then, the old electrolytic solution held on the electrolytic solution holding surface 21 drops as a cleaning solution, and the new electrolytic solution is held on the electrolytic solution holding surface 21 for updating the gas reception portion 23. Therefore, in the vapor phase sensor, the gas reception portion 23 is updated by the operation of supplying a new electrolytic solution, enabling the next measurement to be made easily. In the example, the technique of blowing air containing a stimulant material against the gas reception portion 28 was used, but a sampled gas can be blown for detecting chemical substances in the gas. Also, the vapor phase sensor is placed in the atmosphere to be measured and electrolytic solutions are replaced, thereby measuring chemical substances in the atmosphere whenever necessary.

[Experimental results]

To check the sensor for function, the following were initially used as stimulant solutions for measuring responses:
1. Acid: Acetic acid (stock solution diluted 1-to 10000-times with water)
2. Alkali: Ammonia (diluted 1000- to 100000-times with water)
3. Alcohol: Ethanol (stock solution diluted 1-to 100-times with water)

Figure 4:
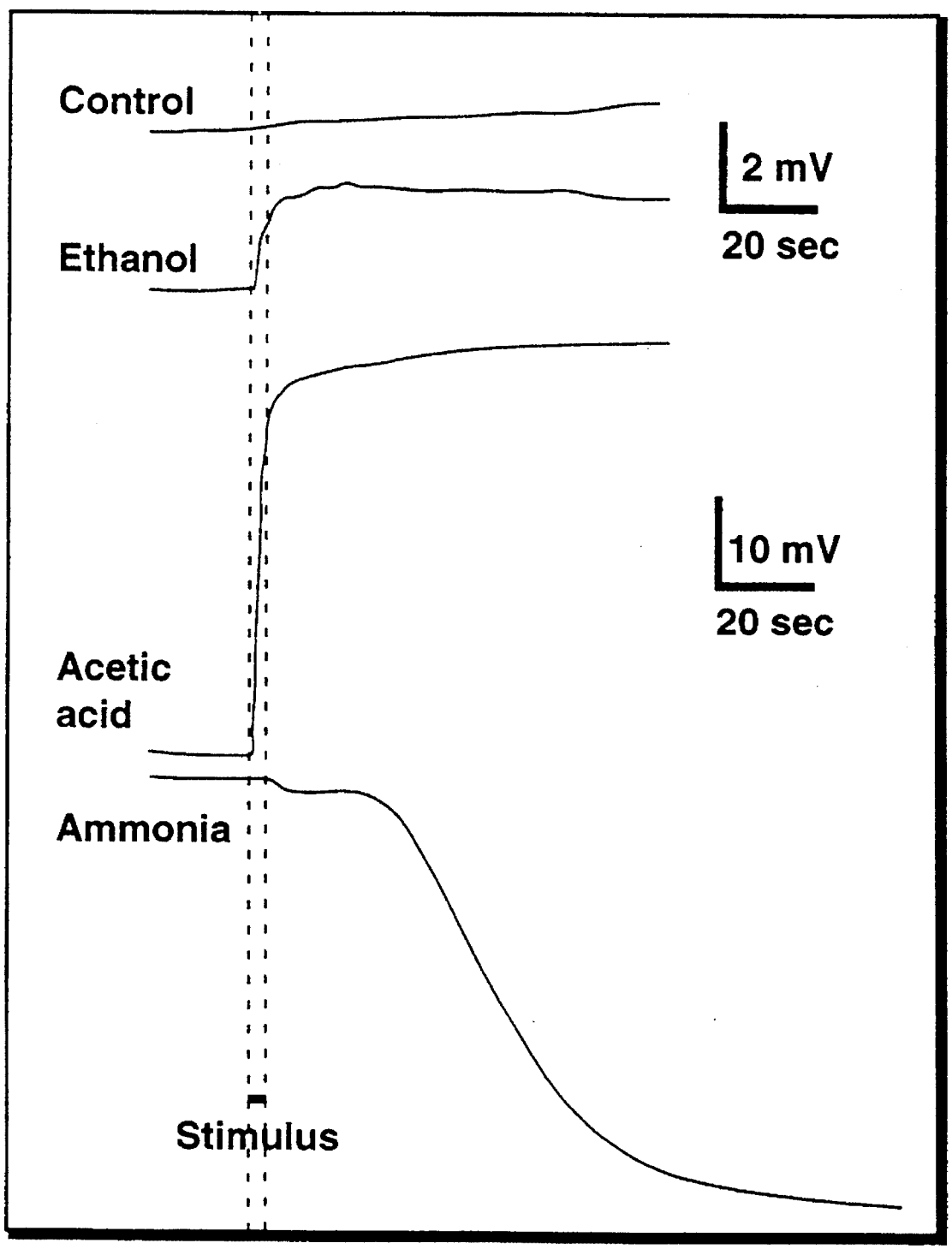
FIG. 4 is a chart showing measurement patterns of substances.

FIG. 4 shows a potential change at the PPy/PVS measurement electrode when control (air flow only), ethanol, acetic acid, and ammonia are blown separately for three seconds. Here, the vertical axis indicates the potential of the measurement electrode and the horizontal axis the time. The measurement results of potential change at the first measurement electrode 20 made of PPy/PVS are shown here.

As shown here, for the control, the potential change is small; for the ethanol, the potential rises about 2 mV rapidly due to stimulation; for the acetic acid, the potential rises about 50 mV rapidly due to stimulation; and for the ammonia, the potential falls about 50 mV gradually due to stimulation. Thus, potential changes proper to the chemical substances appear on the first measurement electrode 20.

Then, if the controller 34 previously stores the patterns of the standard specimens, chemical substances in a vapor phase can be specified by pattern matching. For composite patterns of a plurality of substances, the chemical substances can be specified if the combination is moderate.

Figure 5:
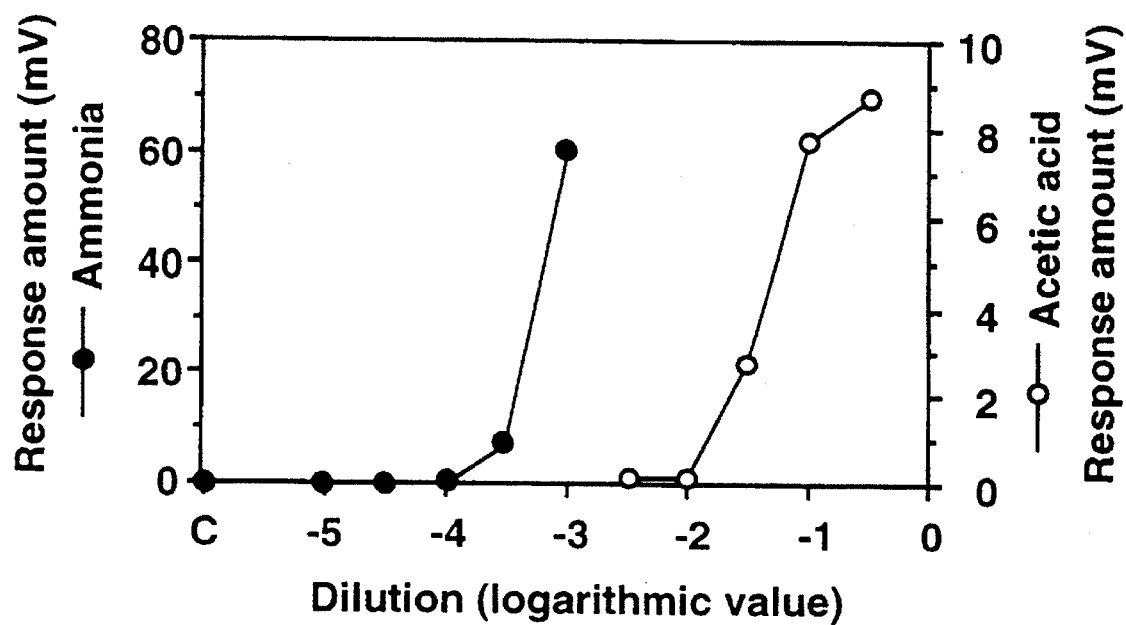
FIG. 5 is a chart showing the relationship between dilution and response amount.

Further, FIG. 5 shows the relationship between dilution (logarithmic expression to the base 10) and response amount (indicating the maximum potential change amount) for acetic acid and ammonia. As shown in the figure, a given relationship exists between the dilution and response amount. Chemical substance amount can also be determined by previously measuring calibration curves. Such determination can also be executed by the controller 34.

Figure 6:
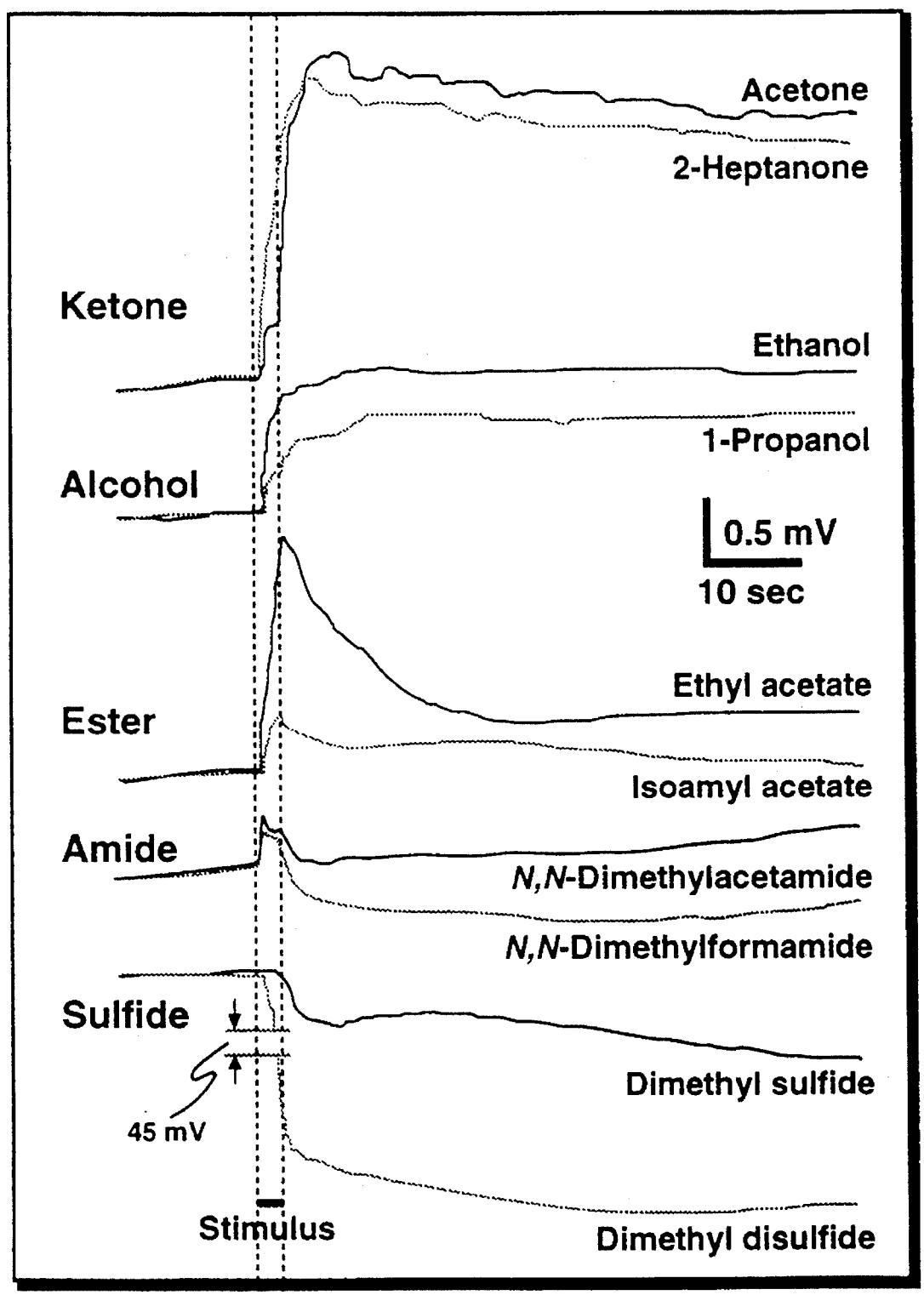
FIG. 6 is a chart showing patterns of response to substances.

Next, the actual measurement results and identification of chemical substances will be described. Two types of substances selected from each of the ketone class, alcohol class, ester class, amide class, and sulfur containing compounds were used as stimulant solutions for detection. Potential responses to the stimulant solutions are shown in FIG. 6. Here, the vertical axis indicates the potential of the measurement electrode and the horizontal axis the time. The stimulation time was three seconds and the first measurement electrode 20 made of PPy/PVS was used as the measurement electrode.

As shown in FIG. 6, potential responses to all substances were obtained. Moreover, the response pattern varies depending on the substance. Thus, if response patterns to various substances are previously measured, the response pattern to the substance being inspected can be compared with the provided patterns for detecting the chemical substance.

The response patterns changing with time for substances having similar chemical structures (the same class) are similar patterns. Therefore, by making an analysis described below, substances can be identified-to some degree; for example, if ethanol is given, it can be identified as a substance being contained in the alcohol class. That is, the method according to the embodiment enables at least identification of a functional group of compounds.

Further, if a number of chemical substances are mixed, the chemical substances can be recognized by predetermined pattern recognition.

Thus, according to the chemical substance detecting method in the embodiment, chemical substances in a vapor phase can be identified, so that odor substances can be identified, for example.

[Pattern analysis]

As described above, odor substances can be identified by comparing the similarity of the pattern of the obtained odor substance to those of the patterns of reference substances previously determined. Such pattern comparison is convenient and easy to determine if it can be quantified. In the embodiment, pattern similarity is quantified routinely according to the procedure described below:

<Reference substances and fitting function>

Figure 7:
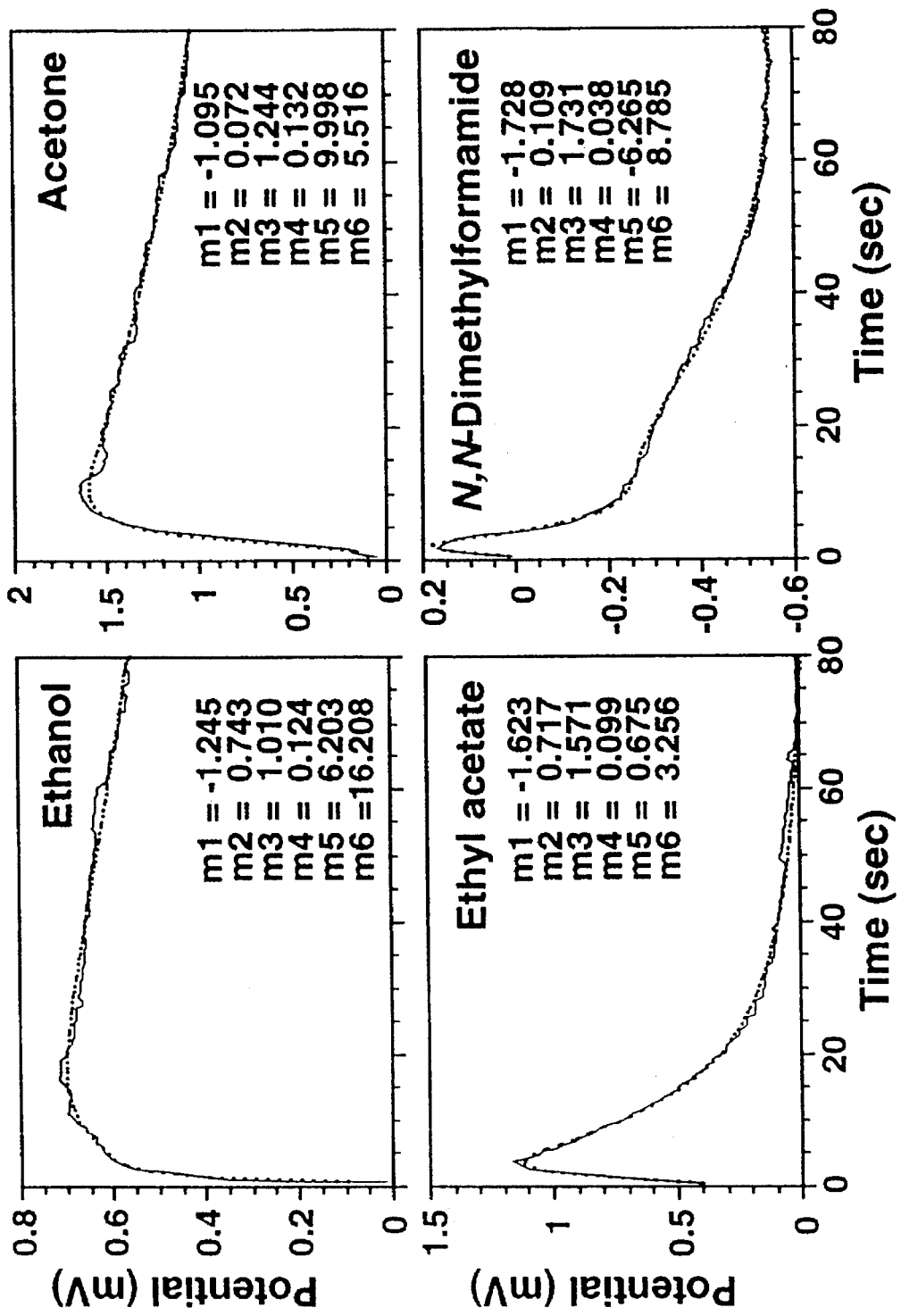
FIG. 7 is graphs showing the fitting results when parameters of reference substances are assigned to a fitting function.

In the embodiment, ethanol, acetone, ethyl acetate, and dimethylformamide were used as reference substances, their patterns of change with time were prepared, and factors common to these substances were considered for setting the fitting function shown below. Therefore, any pattern of the four substances can be prepared by selecting proper parameters of the fitting function (FIG. 7).

Fitting funciton $$y = m1 \cdot e^{-m2 \cdot t} + m3 \cdot e^{-m4 \cdot t} + \frac{m5}{\sqrt{t}} \cdot e^{-m6 \cdot t}$$

Figures 8, 9:
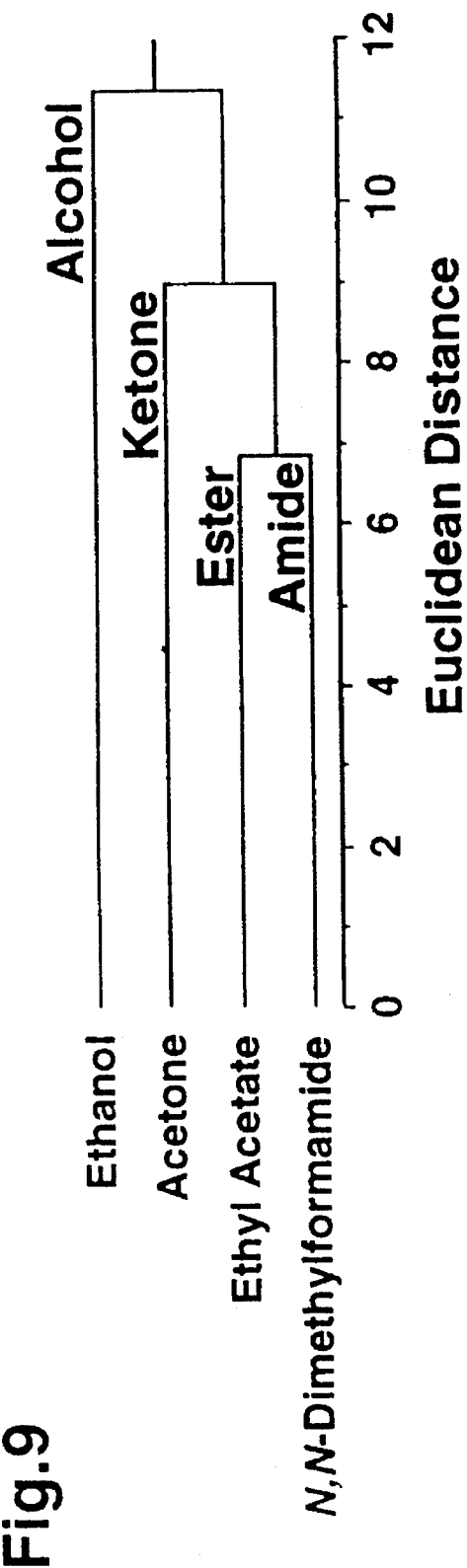
FIG. 8 is a drawing showing the contents of a data base storing parameters.
FIG. 9 is a chart showing a classification example of reference substances using cluster analysis.

In the embodiment, further, a parameter specified when the fitting function is set, which will be hereinafter called the primary parameter, is processed for an analysis to prepare new parameters, called secondary parameters, and a similarity among the chemical substances is determined based on the parameters (FIG. 8). In the embodiment, since the primary parameter contains factors requiring a relative comparison, they are normalized to prepare the secondary parameters. In the embodiment, the primary parameters are stored in a data base (see FIG. 8).

<Determination of degree of similarity, using cluster analysis>

In the embodiment, the degree of similarity is determined by conducting a cluster analysis, as described below: Since the number of the secondary parameters specified in the embodiment is five, a Euclidean distance on the fifth dimension is calculated and is assumed to be the Euclidean Distance. Specifically, the shorter the distance between chemical substances, the higher the Euclidean Distance therebetween. As shown in FIG. 9, according to the analysis, it is found that the Euclidean Distance between ethyl acetate and dimethylformamide is about 7 and moreover that they are chemical substances most similar to each other. Further, the Euclidean Distance of acetone to ethyl acetate or dimethylformamide, whichever is the closer, is about 9. The Euclidean Distance of ethanol to acetone, ethyl acetate, or dimethylformamide, whichever is the closer, is about 11.

In the embodiment, ethyl acetate is selected as a typical substance of the ester class, dimethylformamide as a typical substance of the amide class, acetone as a typical substance of the ketone, and ethanol as a typical substance of the alcohol. So long as the results in FIG. 9 are seen, a generalization may be made such that the Euclidean Distance between ester and amide is the shortest and that ester or amide is more similar to ketone than to alcohol. This suggests that chemical substances can be classified according to the type of functional group that the chemical substances have.

In the embodiment, the Euclidean distance calculation method is adopted as the distance calculation method between parameters (measurement method), but the calculation method is not limited to this method; in addition, a squared Euclidean distance, Chebychev distance, or 1-correlation coefficient calculation method can also be adopted.

<Identification examples of chemical substances>

Figure 10:
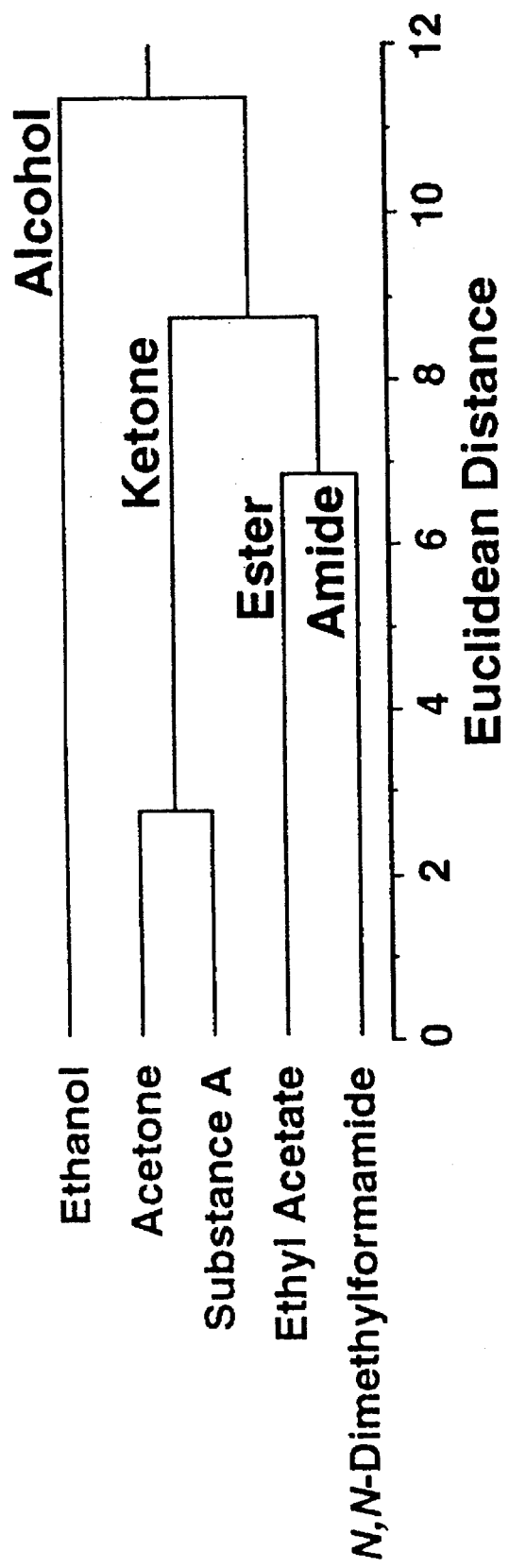
FIG. 10 is a chart showing identification example 1 using cluster analysis (example of identifying chemical substance A)

Next, an example of identifying substance A to be measured is given with reference to FIG. 10. In the example, 2-heptanone is used as substance A. When parameters of substance A are calculated and the Euclidean distances between the parameters and the parameters of each reference substance (ethanol, acetone, ethyl acetate, and dimethylformamide) are found, a value of about 2.8 is obtained with respect to acetone and larger values are obtained with respect to other reference substances. Therefore, it is found that substance A is a compound that is most similar to acetone among the reference substances and moreover that Euclidean Distance substance A to acetone is about 2.8. This result shows the fact that substance A is a substance similar to acetone, and suggests that the chemical group of substance A is likely to be the ketone as mentioned above. In the example, this estimation is correct because substance A is actually 2-heptanone. It can also be found that the Euclidean Distance between the cluster [acetone, substance A] and cluster [ethyl acetate, dimethylformamide] is about 9. Thus, it is also useful to consider the fact for determining the chemical structure of substance A.

Figure 11:
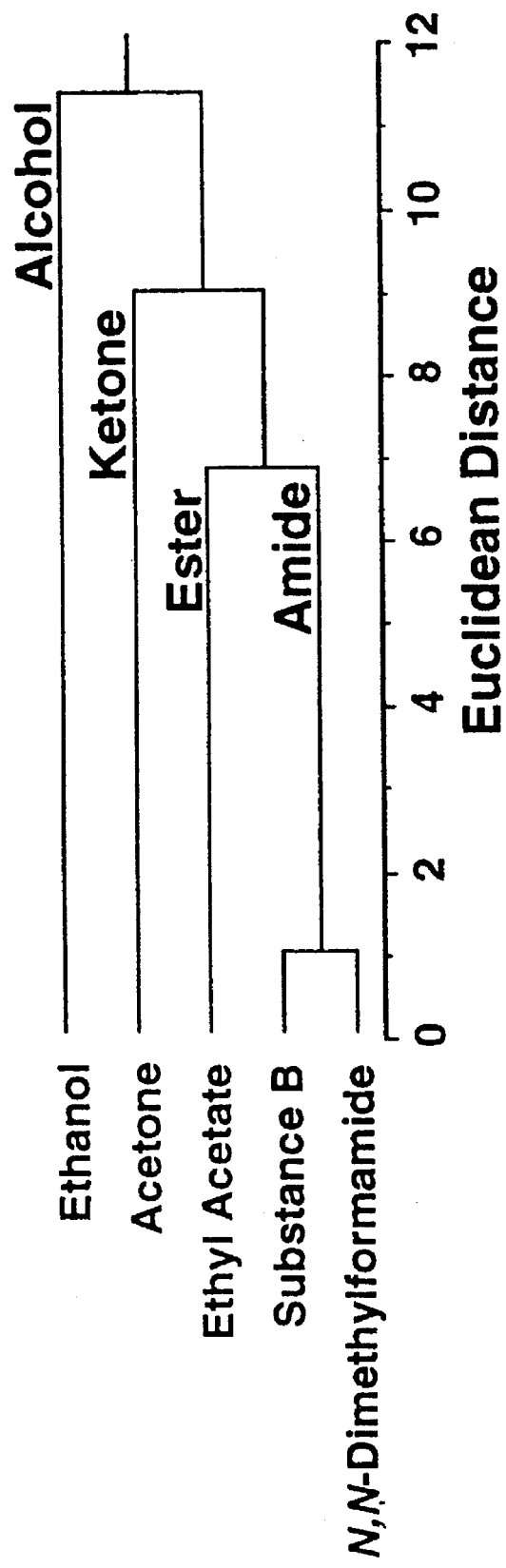
FIG. 11 is a chart showing identification example 2 using cluster analysis (example of identifying chemical substance B)

If dimethylacetamide is used as substance B in identification example 2 (FIG. 11), it is determined that substance B is a substance that is the closest to dimethylformamide. That is, the parameters of substance B are the closest to those of dimethylformamide and moreover the Euclidean distance therebetween is about 1.

<Update of data base>

Figure 12:
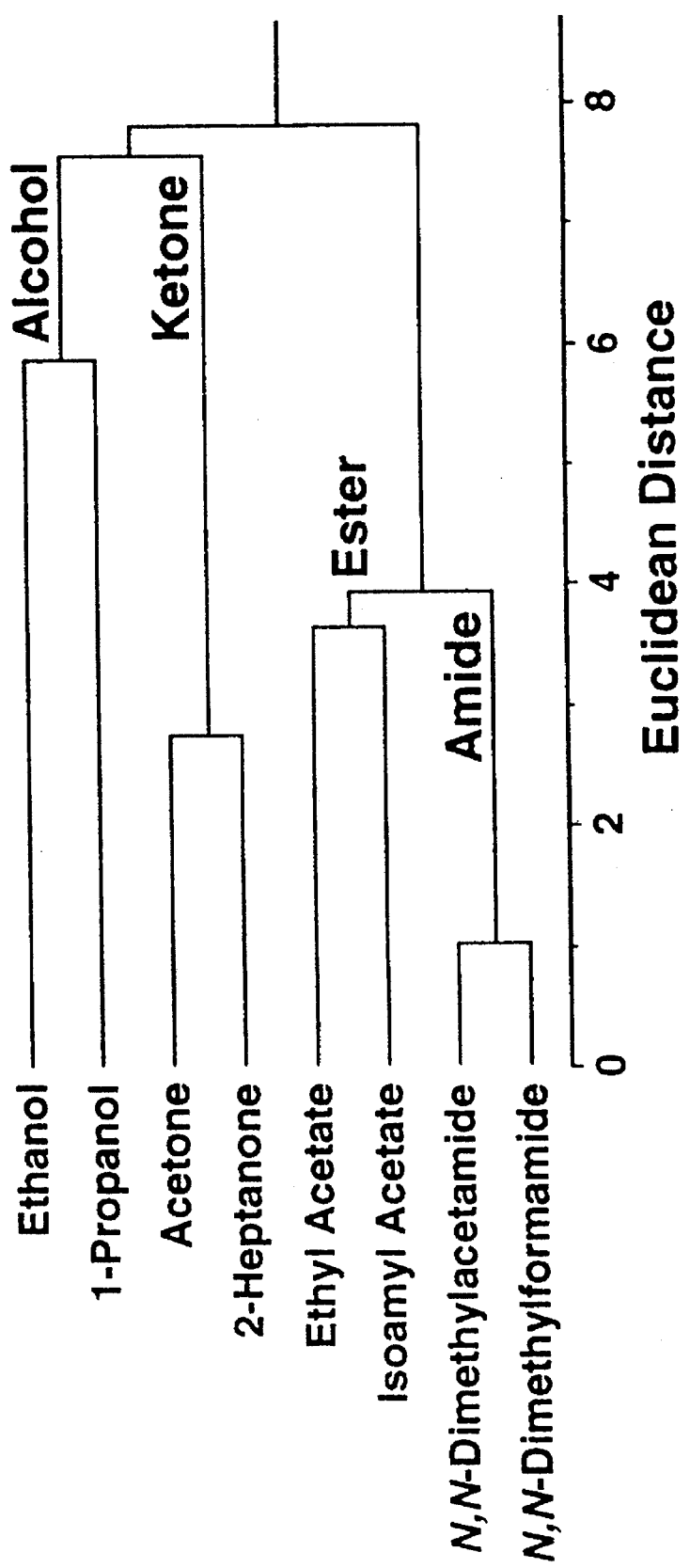
FIG. 12 is a chart for illustrating update of a data base (update by addling data to the database)

The data base can be updated. For example, 1-propanol in addition to ethanol as an alcohol, 2-heptanone in addition to acetone as a ketone, isoamyl acetate in addition to ethyl acetate as an ester, and dimethylacetamide in addition to dimethylformamide as an amide, can be added as data. If ethanol and 1-propanol are added as data, in addition to identification of the substance being measured as a probable alcohol, which of ethanol and 1-propanol the substance is close to can also be specified. For example, if the substance being measured is methanol, it is identified as a substance closer to ethanol than to 1-propanol, and if 1-butanol is measured, it is identified as a substance closer to 1-propanol than to ethanol. Identification of chemical substances can be made in more detail by adding data for updating the data base in such a manner (FIG. 12).

[Film composition difference and response pattern difference between electrodes]

Figure 13:
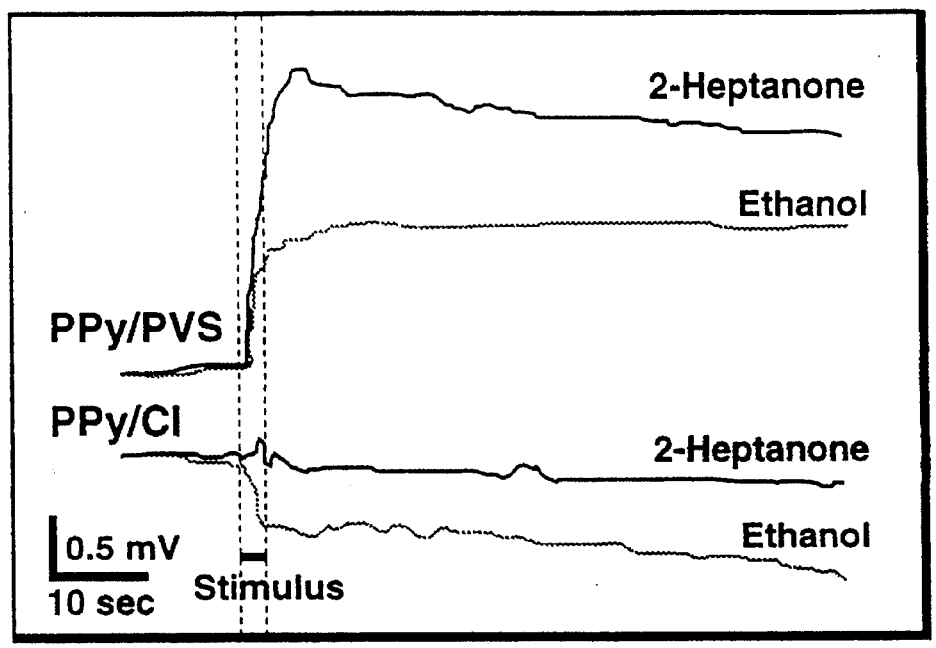
FIG. 13 is a chart showing response patterns which vary depending on the type of films attached on the measurement electrode.

FIG. 13 shows response patterns of the two measurement electrodes (PPy/PVS and PPy/Cl) 20 and 22 to the same substances (in this case, 2-heptanone and ethanol).

As seen in FIG. 13, the PPy/PVS film responds to 2-heptanone in the positive direction of potential, but the PPy/Cl film does not show a remarkable response to 2-heptanone. The PPy/PVS film responds to ethanol in the positive direction, but the PPy/Cl film responds to ethanol in the negative direction.

Thus, different responses to the same chemical substance can be obtained by changing the type of measurement electrode, namely, the type of electrochemically polymerized film. It is considered that the response difference reflects the physicochemlcal property difference between electrochemically polymerized films. Electrochemically polymerized films show physicochemlcal properties varying depending on ions with which the films are doped. Therefore, if response characteristics of more varying types of films are previously examined and a vapor phase sensor provided with a number of measurement electrodes made of the films is used, accuracy of chemical substance identification can be increased. Further, if a number of chemical substances are mixed, their analysis and identification are also facilitated.

[Response amounts to substances]

Not only the response pattern but also the peak potential change amount varies depending on the substance. Therefore, the peak potential change amount as well as the response pattern becomes a substance identification parameter. In the specification, the potential change amount at the peak is represented as "response amount."

Figure 14:
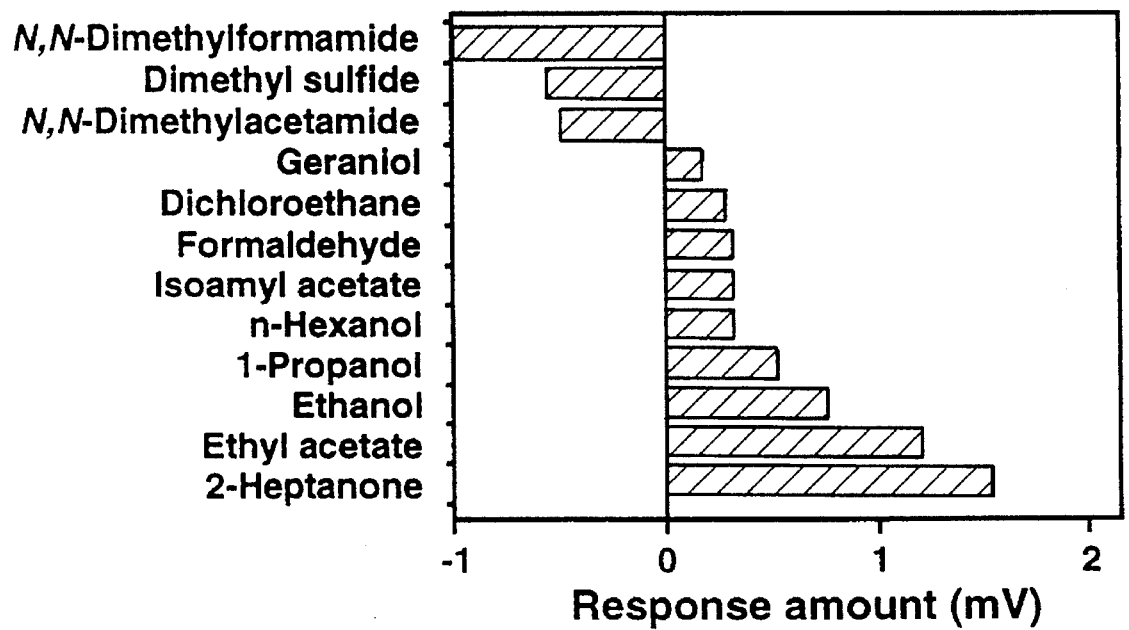
FIG. 14 is a graph showing response amounts to various substances.

FIG. 14 shows the response amounts to various substances. Since the response amount varies depending on the substance, it can be used to detect a specific chemical substance.

Figure 15:
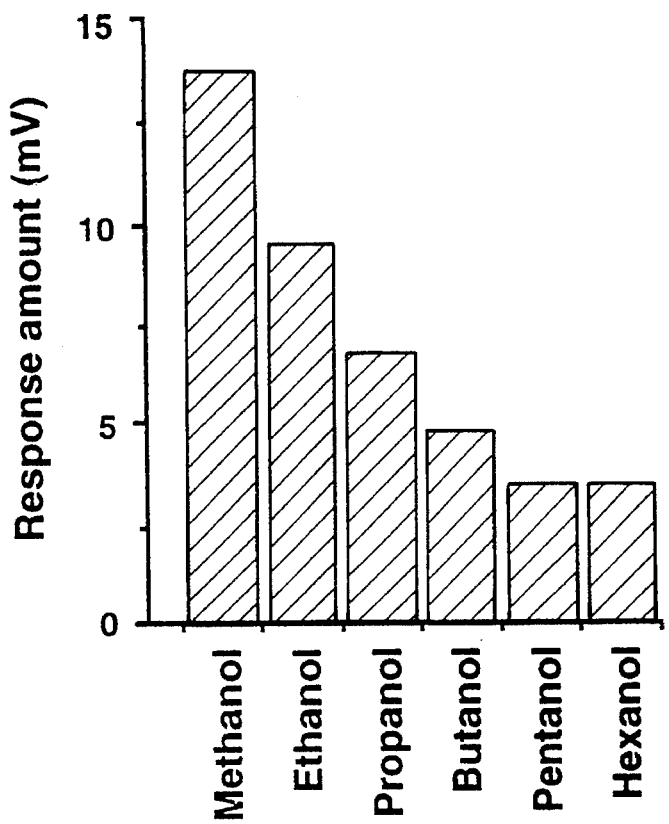
FIG. 15 is a graph showing response amounts to various alcohols.

Further, FIG. 15 shows the response amounts to alcohols having different numbers of carbon atoms. As shown here, the greater the number of carbon atoms, the smaller the response amount to the alcohol. It is considered that solubility in electrolytic solution is reflected. Then, it may be possible to cover chemical substances having a large number of carbon atoms (or high molecular weight) by changing the composition of an electrolytic solution. For example, if such a solvent in which a hydrophobic substance dissolves is used, a substance having a large number of carbon atoms becomes soluble and therefore may be easily detected.

Figure 16:
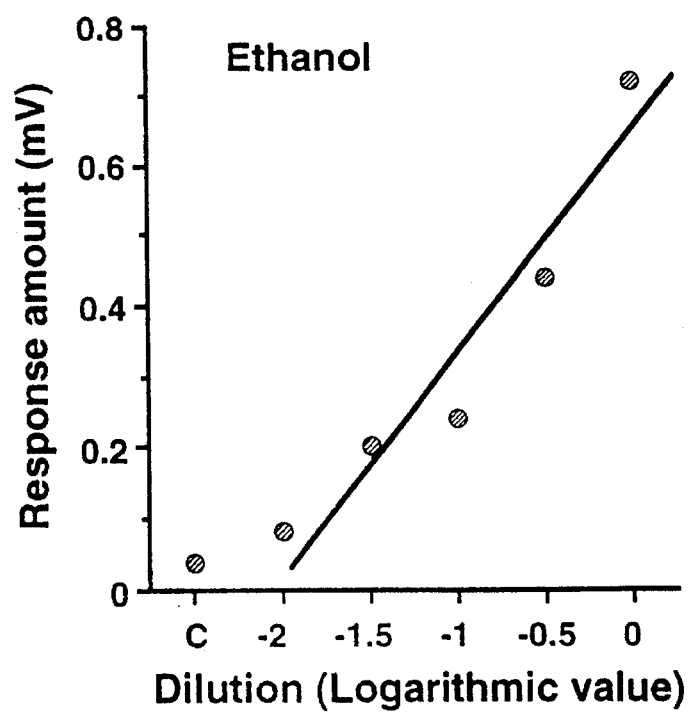
FIG. 16 is a graph showing the relationship between ethanol concentration and response amount.

FIG. 16 shows the measurement results using 100 µl of a solution comprising ethanol diluted with pure water as a stimulant liquid. The vertical axis indicates the maximum response amounts and the horizontal axis indicates dilution magnification with logarithms. As understood from the measurement results, the sensor in the embodiment responds substantially in direct proportion to the concentration. Therefore, the nature can also be used to determine substances.

Here, the potential change measurement results shown in FIGS. 14–16 are all provided by measurement of the first measurement electrode 20 made of PPy/PVS.

[Preparation of measurement electrodes]

Figure 17:
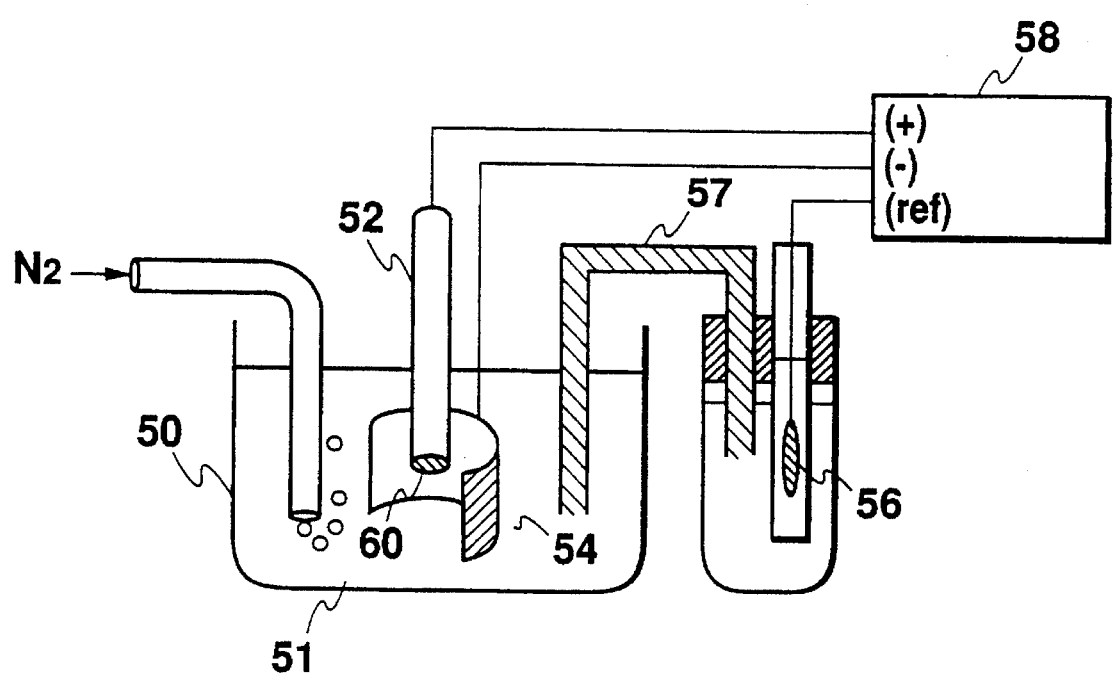
FIG. 17 is a drawing for illustrating preparation of an electrochemically polymerized film.

Next, preparation of electrochemically polymerized films at the measurement electrodes 20 and 22 is described with reference to FIG. 17. A desired monomer solution 51 is contained in a vessel 50 and a working electrode 52, such as a platinum electrode, for which an electrochemically polymerized film is to be prepared and a counter electrode 54 are inserted in the inside of the vessel 50. The working electrode 52 is formed like a cylinder and the counter electrode 54 is formed like a hollow cylinder having a part opened surrounding the working electrode 52. The monomer solution 51 is connected via a salt bridge 57 to a reference electrode 56. The working electrode 52, the counter electrode 54, and the reference electrode 56 are connected to a power supply 58. A nitrogen gas is introduced into the vessel 50.

To form an electrochemically polymerized film, first the monomer solution 51 is stirred with the nitrogen gas to remove dissolved oxygen. Next, while the working electrode 52 is held at a constant potential with respect to the counter electrode 56, a desired current is made to flow from the power supply 58 with the working electrode as a positive pole and the counter electrode as a negative pole for forming an electrochemically polymerized film 60 on the surface of the working electrode 52. Here, a constant potential method, whereby the potential between the working electrode 52 and the counter electrode 54 is controlled so that a desired constant potential exists between the working electrode 52 and the reference electrode 56, or a constant current method, whereby a desired constant current is made to flow between the working electrode 52 and the counter electrode 54 so that a desired constant potential exists between the working electrode 52 and the reference electrode 56, can be used as the voltage applying method.

Thus, the monomer, which is activated by holding the potential of the working electrode 52 at a predetermined potential, such as 0.6 V, or more with respect to the reference electrode 56, is deposited on the working electrode 52 to form a polymer. Since the polymer is conductive, a new polymer is laminated on that polymer if application of potential is continued, so that the electrochemically polymerized film 60 of a thickness matching the applied electricity quantity is formed.

Here, the preparation conditions of the electrochemically polymerized films used in the embodiment are listed:

Monomer solution

For electrochemically polymerized film PPy/PVS aqueous solution of 0.1 M pyrrole+ 0.1 M polyvinyl potassium sulfate For electrochemically polymerized film PPy/PVS aqueous solution of 0.1 M pyrrole+ 0.1 M KCl Electrodes:

Working electrode (+):Platinum disk 1 mm in diameter (area $0.00785$ cm$^2$)

Counter electrode (−):Platinum plate

Electrochemically polymerization condition:Constant current electrolysis 2.5 mA/cm$^2$ Electricity quantity:For example, films having the following thicknesses can be obtained. When they were used for making an experiment, the thinner films were good in sensitivity, but stability of measurement potential worsened. It was found that film thicknesses 0.25 to 2.5 C/cm$^2$ are preferable.

Film thickness 1 (0.25 C/cm$^2$, polymerization time 1 min 40 sec)

Film thickness 2 (1.0 C/cm$^2$, polymerization time 6 min 40 sec)

Film thickness 3 (2.5 C/cm$^2$, polymerization time 16 min 40 sec)

Film thickness 4 (105 C/cm$^2$, polymerization time 66 min 40 sec)

Thus, when pyrrole becomes polypyrrole, anions in the monomer solution (PVS$^-$ and Cl$^-$) are taken in. Since Polarons exist stably in the polymer because of the presence of the anions in the polymer matrix, the polarons function as carriers, thereby making the polymer conductive. The physical property of the electrochemically polymerized film varies depending on the type of anion.

The following merits are provided by using polypyrrole:
1. Films can be easily formed by electrochemical polymerization;
2. films can be fixed on electrodes as conducting thin films;
3. film thickness can be controlled electrochemically; and
4. replacement of dopants is easy and a proper dopant can be selected according to the measurement object.

Here, thiophene and its derivatives in addition to pyrrole, can be used as the monomers for forming the electrochemically polymerized films, sodium paratoluenesulfonate (TsONa), quarternary alkyl ammonium nitrate ($R_4NNO_3$), etc., in addition to potassium chloride can be used as the supporting electrolytes, and acetonitrile, propylene carbonate, etc., in addition to water can be used as the solvents.

As described above, according to the chemical substance detection method of the invention, chemical substances can be identified from patterns detected by a single measurement section. Further, measurement can be repeated by updating the electrolytic solution.

Second embodiment:

The vapor phase sensor according to the invention is characterized by the fact that the surface tension of an electrolytic solution is used to hold the electrolytic solution on the electrolytic solution holding surface 21. In the first embodiment, the electrolytic solution is dropped from the holding surface 21 for updating by supplying another electrolytic solution after measurement has been made. In a second embodiment of the invention, independent means for removing an electrolytic solution from the holding surface 21 is provided as a feature. Components identical with or similar to those previously described in the first embodiment are denoted by the same reference numerals in the description to follow and will not be discussed again.

Figure 18A:
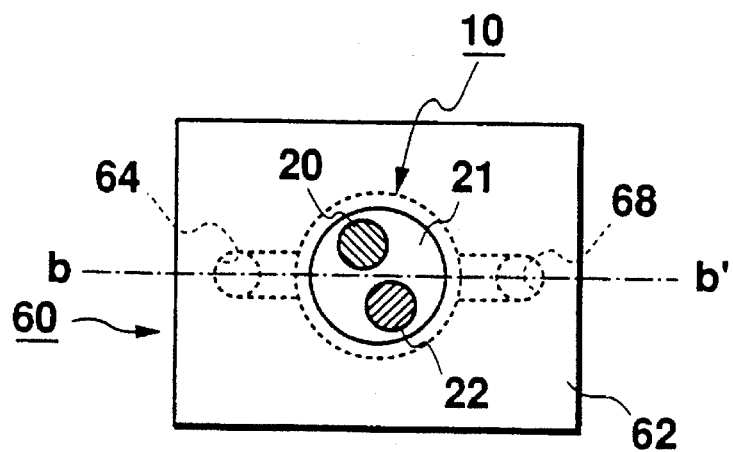
FIGS. 18(a), 18(b), and 18(c) are drawings showing the structure of a vapor phase sensor according to a second embodiment of the invention.
Figures 18B, 18C:
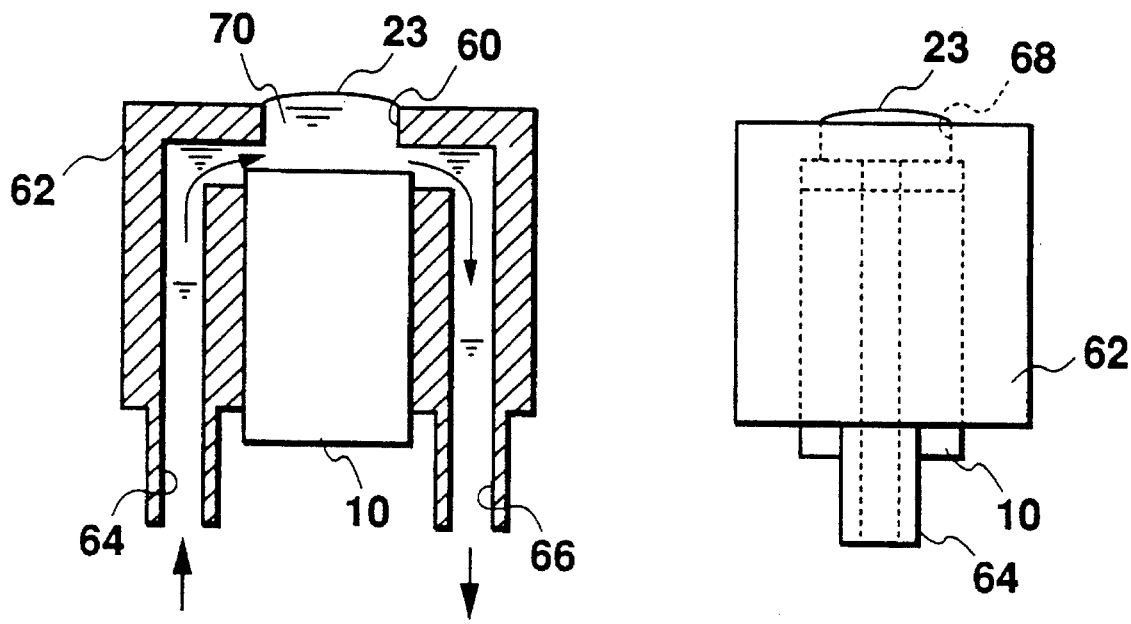

A vapor phase sensor 60 according to the second embodiment of the invention has a measurement section 10 mounted on a base 62, as shown in FIG. 18 (a). The measurement section 10 comprises a first and second measurement electrodes 20 and 22, as in the first embodiment. The vapor phase sensor 60 is provided with a supply pipe 64 and a discharge pipe 66, as shown in FIG. 18 (b)(c), a sectional view of the sensor 60. A reference electrode 26 may be placed in any position electrically communicated with the measurement electrodes in an electrolytic solution; here, the reference electrode 26 (not shown) is disposed within the supply pipe 64 or the discharge pipe 66. An electrolytic solution supplied from the supply pipe 64 is stored in a recess 68 made on the base 62. The electrolytic solution stored in the recess 68 is discharged from the discharge pipe 66. If the electrolytic solution is supplied with its discharge stopped, a drop 70 is formed on the recess 68 by its surface tension and the surface of the drop 70 forms a gas reception portion 23 as it is. The supply pipe 64 and the discharge pipe 66 are placed coaxially with each other, as shown in FIG. 18 (*a*).

The structure of the vapor phase sensor according to the second embodiment enables accurate control of the surface area and volume of the gas reception portion 23, thus providing the advantage of improving the quantitative property of the vapor phase sensor. Also, when the electrolytic solution is updated, the solution does not scatter to the outside. Thus, the gas reception portion 23 can be installed in any direction without being fixed downward as in the sensor according to the first embodiment.

To identify a chemical substance in a mixed gas containing a plurality of chemical substances or raise the identification accuracy of chemical substances, a number of sensors having different response characteristics need to be used for measurement. To construct a multisensor consisting of a number of sensors, the structure according to the second embodiment is also useful. The type of electrochemically polymerized film and the type of electrolytic solution are factors for changing the response characteristics of the vapor phase sensor. The number of electrodes installed in the measurement section 10 can be set freely in response to the measurement object. The type of electrochemically polymerized film can be changed. Since the supply and discharge pipes of an electrolytic solution are mounted on the base 62 in the second embodiment, a number of vapor phase sensors are connected to separate supply and discharge channels of electrolytic solutions, whereby a multisensor can also be provided for changing the type of electrolytic solution. In fact, if both the film and electrolytic solution types are optimized in response to the measurement object, a more effective multisensor can be provided.

Thus, the vapor phase sensor according to the embodiment can detect a chemical substance in a vapor phase diffusing into an electrolytic solution held on the electrolytic solution holding surface 21 as a potential change at the electrodes in the electrolytic solution.

As described above, according to the vapor phase sensor of the invention, the surface of an electrolytic solution is exposed directly to the air. Then, odor substance, etc., in a vapor phase can be efficiently diffused into the electrolytic solution; stable and accurate detection can be made. Particularly, a substance can be accurately specified by analyzing a change pattern of the electric state detected (change with time). Further, the electrolytic solution can be easily updated, so that detection can be executed whenever necessary. Also, high-performance detection can be maintained over a long term by making the measurement electrodes of electrochemically polymerized films.

Freshness measurement of beef

[Measurement operation]

Figure 19:
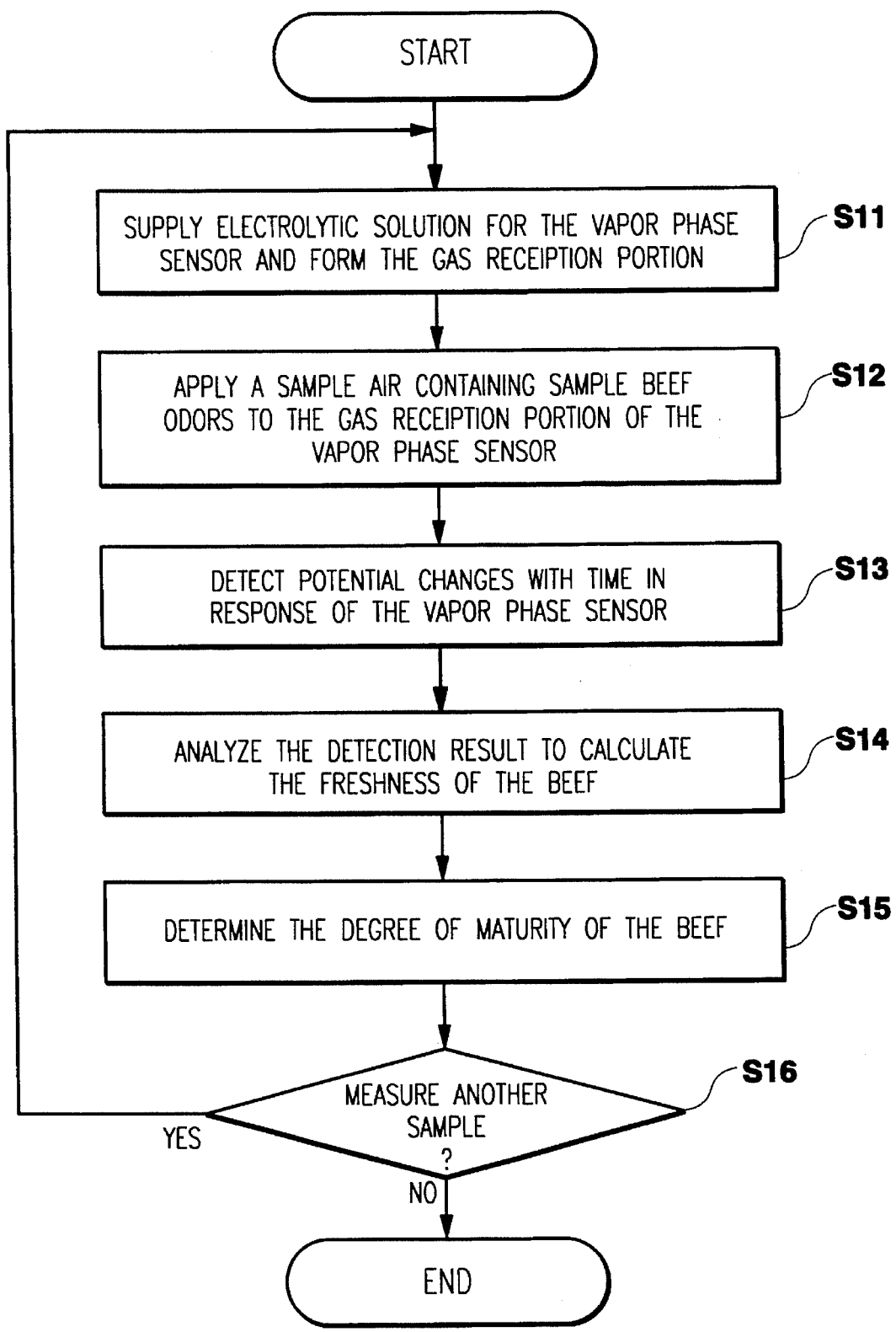
FIG. 19 is a flowchart showing the measurement operation of the vapor phase sensor according to the second embodiment of the invention.

An example of detecting the degree of maturity of beef will be described with reference to FIG. 19 as one example of a food stuff freshness measurement method using the vapor phase sensor having the above-mentioned structure. First, a predetermined amount of an electrolytic solution is supplied from an electrolytic solution reservoir 28 and is held on the electrolytic solution holding surface 21 for forming the gas reception portion 28 at step S11.

Next, a gas containing odor substances discharged from beef being inspected is blown against the gas reception portion 28 at step S12. This step is performed, for example, as follows: First, 100 µl of extracted juice from the beef being inspected is measured and is dropped on deodorized filter paper 40 (area 5 cm$^2$). The filter paper 40 is housed in a Pasteur pipette 42 and the rear end of the Pasteur pipette 42 is connected via an odorless tube (not shown) to a pump (not shown).

In this condition, air is fed from the pump to blow the gas containing odor substances discharged from the beef, evaporating from the filter paper 40 against the gas reception portion 23 of the vapor phase sensor. The stimulation time for which the gas is blown was 1–20 seconds at flow velocity 90 ml/min (air velocity 1.9 m/sec). The stimulation time 1s controlled by a controller 34. The flow velocity may be monitored with a flow meter and be feedback controlled by the controller 34. A deodorizing tube containing activated carbon and a dehydrating tube containing silica gel are located between the pump and the pipette for using air from which odors and water vapor are removed.

The potential difference between the measurement electrodes 20, 22 and the reference electrode 26 is detected on a recorder at step S13. The detection result is sent to the controller 34, which then analyzes the detection result to calculate the freshness of the beef at step S14. The degree of maturity is determined based on the calculation result at step S15.

To continue subsequent measurement at step S16, a new electrolytic solution is supplied.

Then, the old electrolytic solution held on the electrolytic solution holding surface 21 is dropped as a cleaning solution. Thus, the new electrolytic solution is held on the electrolytic solution holding surface 21 for updating the gas reception portion 28. In the example, the technique of soaking the filter paper with the beef juice and blowing air passed through the filter paper against the gas reception portion 23 was used, but a gas containing odor substances sampled from the food stuff (beef) can be blown for measuring the freshness of the food. Also, the gas reception portion 23 may be placed in the atmosphere to be measured for measuring at predetermined timing.

[Experimental results]

Next, the actual experiment results will be discussed with reference to FIG. 20. In the experiment, gases containing odor substances discharged from beef samples having different numbers of storage days were measured as described above. In the experiment, the storage temperature was 23° C. and PPy/PVS films were used on the surface of measurement electrodes.

Figure 20:
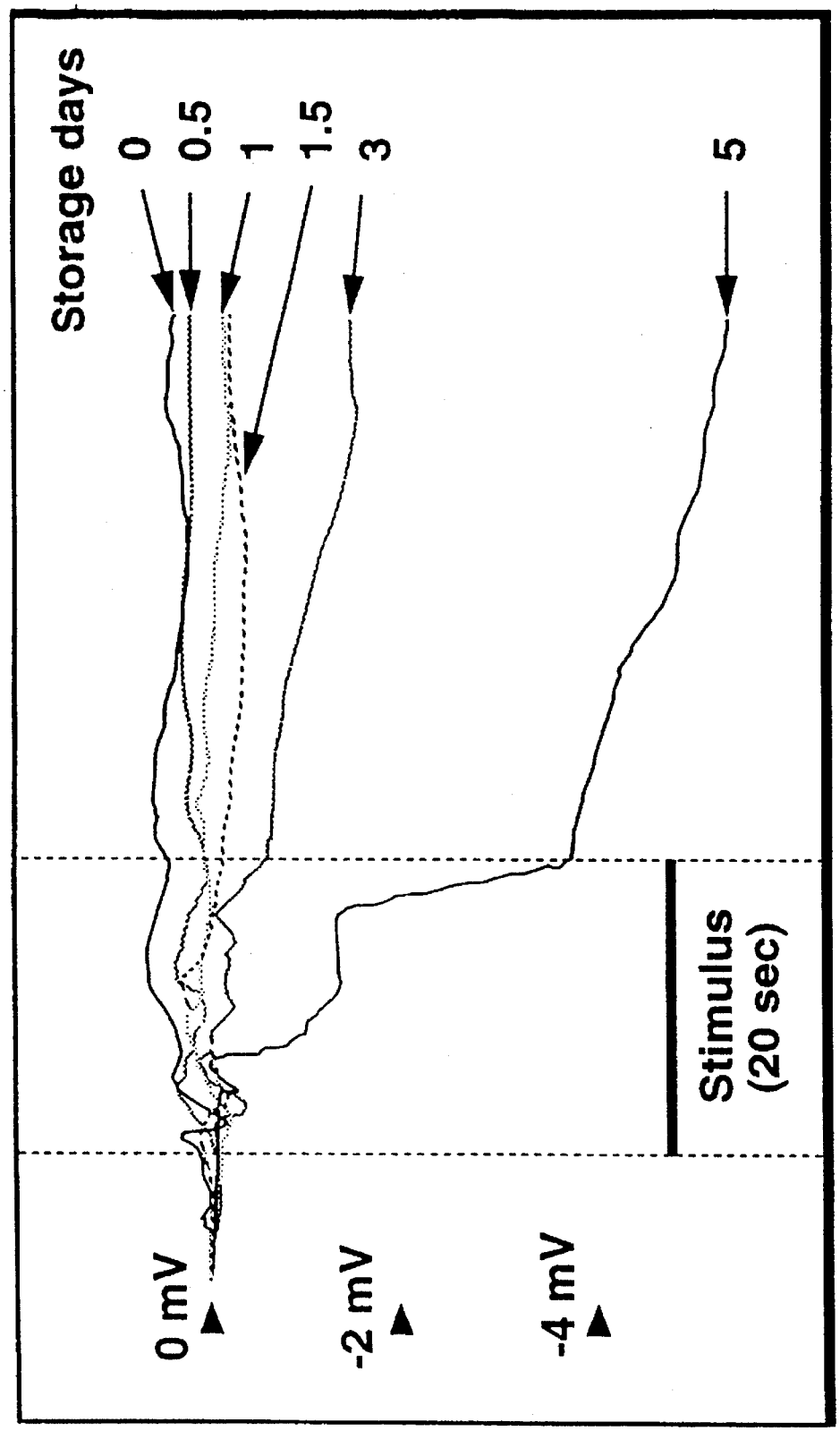
FIG. 20 is a chart showing response patterns to beef of different maturity degrees.

Under these conditions, each gas was blown against the gas reception portion 23 for 20 seconds indicated by the solid line in FIG. 20. As shown here, when the number of storage days is 0, a response in the positive direction is observed; as the number of storage days increases, a response changes from the positive direction to the negative direction with a larger response amount, and response patterns also vary. It is considered that these reflect the fact that the amounts and types of chemical substances (odor substances) discharged into the vapor phase from the beef vary with the number of storage days.

Therefore, if the features of the response patterns are previously extracted, freshness of beef can be calculated by analyzing a response of the vapor phase sensor, thereby determining the maturity degree.

Figure 21:
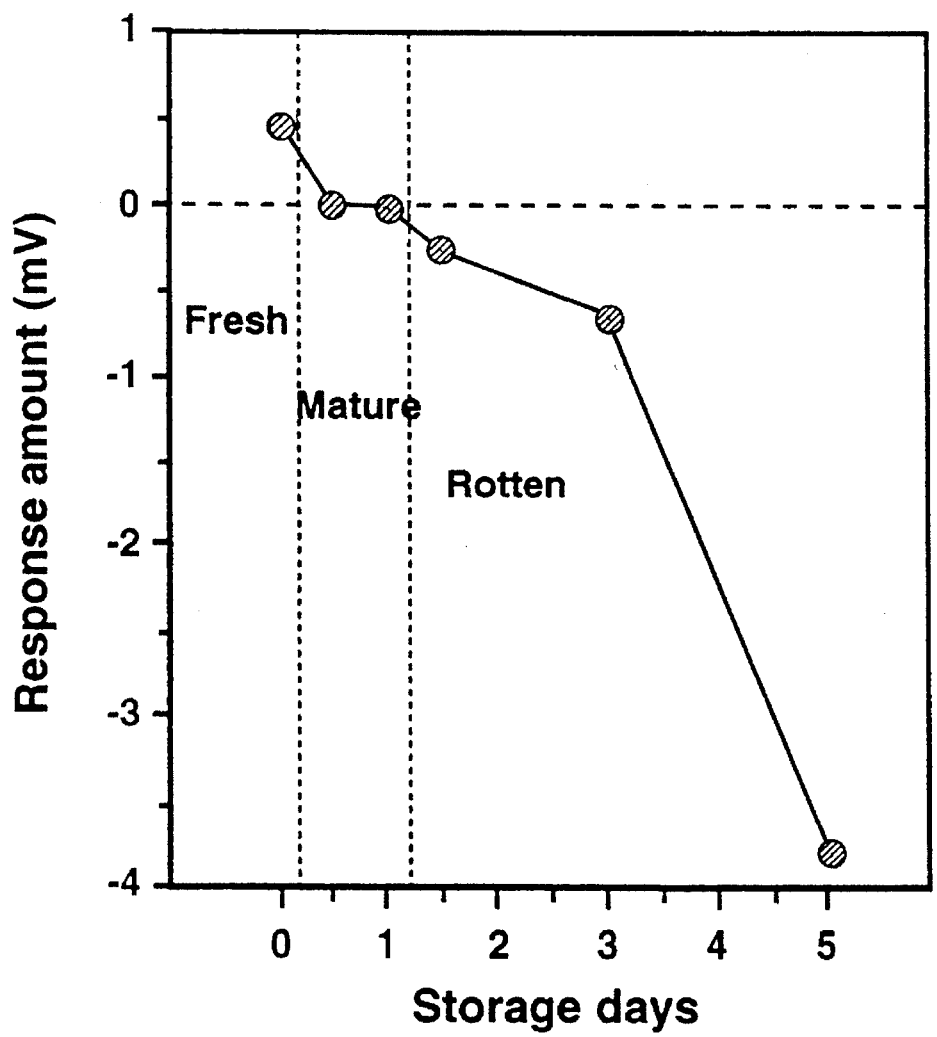
FIG. 21 is a graph showing the relationship between the number of storage days and response amount.

FIG. 21 shows the relationship between the number of storage days and the response amount of the sensor. In the figure, Fresh denotes not yet tasty (unmatured) beef; Mature denotes mature and edible beef; and Rotten denotes unedible beef. For the response amount, the potential change amount at the end of stimulation for 20 seconds was adopted. The response to the fresh beef stored for 0 days is made in the positive direction, and the response to the mature beef (stored for 0.5, 1 day) is 1. The response to the rotten beef (stored for 1.5 days) is made in the negative direction.

Therefore, the degree of maturity of beef can be measured by such measurement. Further, the features of response patterns as shown in FIG. 20 are extracted, reference values are preset, and the degree of maturity is determined based on the patterns, thereby determining it more accurately.

Freshness of beef can also be measured with the vapor phase sensor according to the second embodiment as with the vapor phase sensor according to the first embodiment.

As described above, according to the food freshness measurement method of the invention, chemical substances contained in a vapor phase are diffused into an electrolytic solution and absorbed on the electrodes, causing the electric state of the electrodes to change, and freshness of food is measured in response to the electric state change of the electrodes. Thus, measurement can be made without human intervention, so that freshness can be measured objectively. Particularly, it was difficult to measure freshness (maturity degree) of beef with conventional measuring instruments, but the invention makes such measurement possible. Preferred beef freshness measurement can be made by using the electrodes made of conducting polymer films.

[Measuring system of chemical substances in vapor phase]

Figure 22:
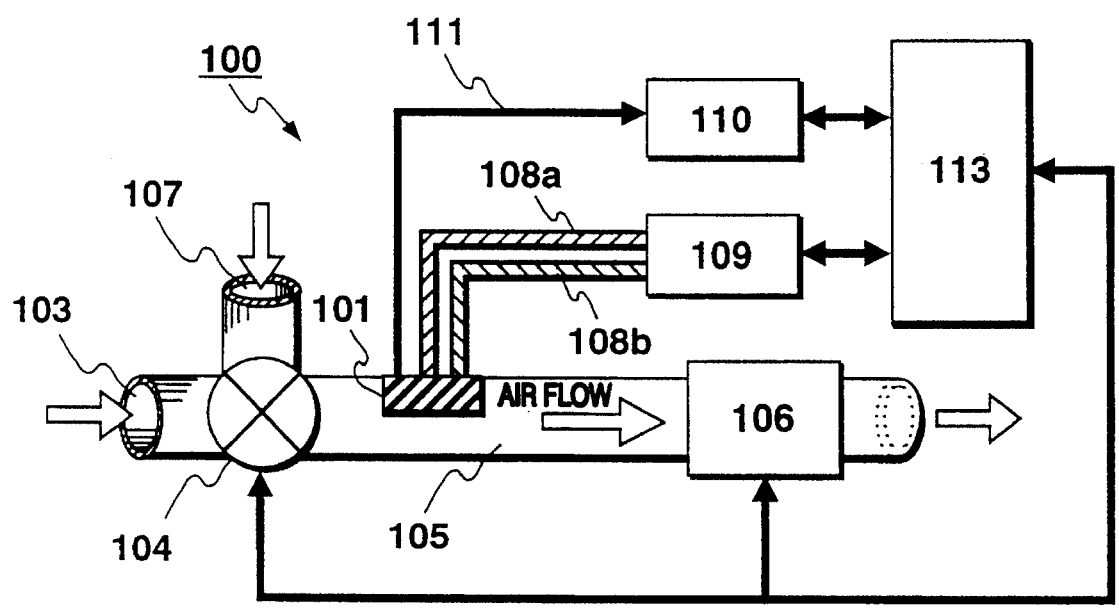
FIG. 22 is a block diagram showing the configuration of an odor measuring system as one example of a measuring system of chemical substances in a vapor phase.

FIG. 22 is a block diagram showing the configuration of an odor measuring system as one example of a system of measuring chemical substances in a vapor phase. The odor measuring system 100 is characterized by the fact that it comprises a vapor phase sensor 101 according to the invention into which the air is led. Either of the vapor phase sensors according to the first and second embodiments can be used for the vapor phase sensor 101. In the odor measuring system 100, the air is sucked in through an air introduction port 108 to introduce it into the vapor phase sensor 101. That is, in the odor measuring system 100 according to the embodiment, the vapor phase sensor 101 is attached to the inside of an air introduction pipe 105 for measuring chemical substances contained in the air sucked through the air introduction port 103, thereby detecting odors. In the embodiment, an air controller 106 is connected to the end of the air suction pipe 105. The air controller 106 comprises an air pump, a flow meter etc., for sucking the air via the air suction pipe 105 from the outside. A solenoid valve 104 is mounted on the air suction port 103 for controlling the on/off operation of air suction and the air suction amount. In the embodiment, the air suction pipe 105 branches to introduce cleaning air. A solenoid valve 104 is also mounted on a cleaning air introduction port 107, and the cleaning air is controlled by opening and closing the solenoid valve 104. A solution controller 109 controls supply and discharge of solutions via the supply pipe 108a and discharge pipe 108b to and from the vapor phase sensor 101. A signal processing display section 110 processes data obtained from the vapor phase sensor 101 and displays the processing result. The signal processing display section 110 and the vapor phase sensor 101 are connected by signal lines 111. The odor measuring system 100 according to the embodiment comprises a control section 113 which controls the entire system. The signal processing and display section 110 performs data processing using the detection method and identification method for chemical substances as described above for specifying chemical substances contained In the air. Particularly, if the system is adopted to detect an odor of beef, it can measure the freshness of beef. The odor measuring system 100 actively sucks the air and leads it into the vapor phase sensor and therefore can also detect a minute amount of odor substance (odor source substance). For example, if the system is installed in a refrigerator, rotten food stuffs stored therein can be detected easily.

What is claimed is:

1. A vapor phase sensor comprising:

(A) measurement electrodes;

(B) a reference electrode;

(C) an electrolytic solution holding surface comprising at least said measurement electrodes and said reference electrode for holding an electrolytic solution having an outer surface exposed directly to a vapor phase on surfaces of said measurement electrodes and said reference electrode by using surface tension thereof;

(D) a source for supplying an electrolytic solution onto said electrolytic solution holding surface; and (E) a section for detecting an electric state change between said measuring electrodes and said reference electrode caused by a chemical substance in a vapor phase diffusing into the electrolytic solution, wherein the electrolytic solution held on said electrolytic solution holding surface is replaced with a fresh electrolytic solution from said source for supplying an electrolytic solution for detecting a further substance in a vapor phase.

2. The vapor phase sensor as claimed in claim 1 further including means for removing an electrolytic solution held on said electrolytic solution holding surface.

3. The vapor phase sensor as claimed in claim 2 wherein the surfaces of said measurement electrodes are made of conducting polymers.

4. The vapor phase sensor as claimed in claim 1 wherein the surfaces of said measurement electrodes are made of conducting polymers.

5. A chemical substance detection system comprising:

(A) measurement electrodes;

(B) a reference electrode;

(C) an electrolytic solution holding surface containing at least said measurement electrodes and said reference electrode for holding an electrolytic solution having an outer surface exposed directly to a vapor phase on surfaces of said measurement electrodes and said reference electrode by using surface tension thereof;

(D) a source for supplying an electrolytic solution onto said electrolytic solution holding surface;

(E) a section for detecting an electric state change between said measuring electrodes and said reference electrode caused by a chemical substance in a vapor phase diffusing into the electrolytic solution; and (F) a mechanism for supplying air to a surface of the electrolytic solution formed on said electrolytic solution holding surface, wherein the electrolytic solution held on said electrolytic solution holding surface is replaced with a fresh electrolytic solution from said source for supplying an electrolytic solution for detecting a further substance in a vapor phase.

6. The detection system as claimed in claim 5 further including means for removing an electrolytic solution held on said electrolytic solution holding surface.

7. The detection system as claimed in claim 6 wherein the surfaces of said measurement electrodes are made of conducting polymers.

8. The detection system as claimed in claim 5 wherein the surfaces of said measurement electrodes are made of conducting polymers.

* * * * *

UNITED STATES PATENT AND TRADEMARK OFFICE
CERTIFICATE OF CORRECTION

PATENT NO.   : 5,545,299
DATED        : August 13, 1996
INVENTOR(S)  : AKIFUMI IWAMA; MASAHIRO ISEKI; AZUSA NAKAGAWA It is certified that error appears in the above-indentified patent and that said Letters Patent is hereby corrected as shown below:

On the title page, under [30] Foreign Application Priority Data, before "Japanese Patent Application No. 5-228611", delete "September 13, 1993" and insert therefor --September 14, 1993--.

Signed and Sealed this

Twenty-sixth Day of August, 1997

Attest:

BRUCE LEHMAN

Attesting Officer

Commissioner of Patents and Trademarks